(12) United States Patent
Weston et al.

(10) Patent No.: US 12,115,266 B2
(45) Date of Patent: Oct. 15, 2024

(54) METHODS AND APPARATUS TO REDUCE BIOLOGICAL CARRYOVER USING INDUCTION HEATING

(71) Applicant: Abbott Laboratories, Abbott Park, IL (US)

(72) Inventors: Brad Weston, Frisco, TX (US); Jeffrey Mitchell, Little Elm, TX (US)

(73) Assignee: Abbott Laboratories, Abbott Park, IL (US)

( * ) Notice: Subject to any disclaimer, the term of this patent is extended or adjusted under 35 U.S.C. 154(b) by 2 days.

(21) Appl. No.: 17/951,837

(22) Filed: Sep. 23, 2022

(65) Prior Publication Data

US 2023/0241260 A1    Aug. 3, 2023

Related U.S. Application Data

(63) Continuation of application No. 15/984,741, filed on May 21, 2018, now Pat. No. 11,452,787, which is a
(Continued)

(51) Int. Cl.
*A61L 2/00* (2006.01)
*A61L 2/04* (2006.01)
(Continued)

(52) U.S. Cl.
CPC .................. *A61L 2/04* (2013.01); *B01L 3/021* (2013.01); *B01L 13/02* (2019.08); *B08B 3/04* (2013.01);
(Continued)

(58) Field of Classification Search
CPC ..................................... A61L 2/00; A61L 9/18
(Continued)

(56) References Cited

U.S. PATENT DOCUMENTS 4,327,268 A    4/1982  Frank
4,492,840 A    1/1985  Lex
(Continued)

FOREIGN PATENT DOCUMENTS

CN    1454318 A    11/2003
CN    2629702 Y     8/2004
(Continued)

OTHER PUBLICATIONS

Japan Patent Office, "Notice of Reasons for Refusal," issued in connection with Japanese Patent Application No. 2022-201866, dated Feb. 27, 2024, 10 pages. [English Translation Included].
(Continued)

*Primary Examiner* — Monzer R Chorbaji
(74) *Attorney, Agent, or Firm* — Hanley, Flight & Zimmerman, LLC

(57) ABSTRACT

Methods and apparatus to reduce biological carryover using induction heating are disclosed herein. An example method includes washing an aspiration and dispense device. The example method includes generating an alternating electromagnetic field and introducing the aspiration and dispense device into the alternating electromagnetic field. The example method includes inductively heating the aspiration and dispense device with the alternating electromagnetic field. In the example method, the washing is to occur in concert with the heating.

20 Claims, 9 Drawing Sheets

Related U.S. Application Data continuation of application No. 15/593,955, filed on May 12, 2017, now Pat. No. 9,974,872, which is a continuation of application No. 14/791,964, filed on Jul. 6, 2015, now Pat. No. 9,686,824, which is a continuation of application No. 13/721,931, filed on Dec. 20, 2012, now Pat. No. 9,073,094.

(60) Provisional application No. 61/580,913, filed on Dec. 28, 2011.

(51) Int. Cl.
    *B01L 3/02*     (2006.01)
    *B08B 3/04*     (2006.01)
    *B08B 7/00*     (2006.01)
    *B08B 7/04*     (2006.01)
    *C25B 5/00*     (2006.01)
    *G01N 21/00*     (2006.01)
    *H05B 6/02*     (2006.01)
    *H05B 6/08*     (2006.01)
    *H05B 6/10*     (2006.01)

(52) U.S. Cl.
    CPC .............. *B08B 7/00* (2013.01); *B08B 7/0071* (2013.01); *B08B 7/04* (2013.01); *H05B 6/08* (2013.01); *H05B 6/101* (2013.01); *H05B 6/108* (2013.01); *A61L 2202/17* (2013.01); *A61L 2202/24* (2013.01); *B01L 2200/141* (2013.01)

(58) Field of Classification Search
    USPC .............. 219/600, 764; 250/453.11, 455.11, 250/492.1; 204/156, 157.15; 422/1, 422/21–22
    See application file for complete search history.

(56) References Cited

U.S. PATENT DOCUMENTS

| | | | |
|---|---|---|---|
| 4,608,472 A * | 8/1986 | Kato | A61L 2/12 219/673 |
| 5,178,019 A | 1/1993 | Keiter | |
| 5,434,389 A | 7/1995 | Griebel | |
| 5,476,634 A | 12/1995 | Bridges et al. | |
| 5,765,490 A | 6/1998 | Colin et al. | |
| 5,965,086 A | 10/1999 | Rose et al. | |
| 6,379,631 B1 | 4/2002 | Wu | |
| 6,582,659 B1 | 6/2003 | Murata | |
| 6,627,163 B1 | 9/2003 | Awakowicz et al. | |
| 6,632,287 B1 | 10/2003 | Colin et al. | |
| 6,692,693 B2 | 2/2004 | Wu | |
| 6,734,405 B2 | 5/2004 | Centanni et al. | |
| 6,756,223 B2 | 6/2004 | Roberts et al. | |
| 6,759,017 B2 | 7/2004 | Wu et al. | |
| 6,906,296 B2 | 6/2005 | Centanni et al. | |
| 6,930,292 B1 | 8/2005 | Winther et al. | |
| 6,967,315 B2 | 11/2005 | Centanni et al. | |
| 7,017,594 B2 | 3/2006 | Kurunczi | |
| 7,094,314 B2 | 8/2006 | Kurunczi | |
| 7,367,344 B2 | 5/2008 | Kurunczi | |
| 7,446,288 B2 | 11/2008 | Boege et al. | |
| 7,507,369 B2 | 3/2009 | Lu | |
| 7,687,045 B2 | 3/2010 | Lu | |
| 7,781,708 B2 | 8/2010 | Wallace et al. | |
| 7,858,908 B2 | 12/2010 | Wallace et al. | |
| 7,927,557 B2 | 4/2011 | Dieras et al. | |
| 7,939,016 B2 | 5/2011 | Lu | |
| 8,092,643 B2 | 1/2012 | Kurunczi | |
| 8,092,644 B2 | 1/2012 | Kurunczi | |
| 8,115,147 B2 | 2/2012 | Thomas et al. | |
| 8,366,871 B2 | 2/2013 | Kurunczi | |
| 8,444,919 B2 | 5/2013 | Erickson | |
| 8,591,807 B2 | 11/2013 | Berentsveig et al. | |
| 8,591,808 B2 | 11/2013 | Berentsveig et al. | |
| 8,658,089 B2 | 2/2014 | Berentsveig et al. | |
| 8,974,737 B2 | 3/2015 | Erickson | |
| 9,011,786 B2 | 4/2015 | Hemphill et al. | |
| 9,073,094 B2 | 7/2015 | Weston et al. | |
| 9,075,042 B2 | 7/2015 | Cook et al. | |
| 9,081,001 B2 | 7/2015 | Cook et al. | |
| 9,101,678 B2 | 8/2015 | Hegg et al. | |
| 9,138,005 B2 | 9/2015 | Berentsveig et al. | |
| 9,162,259 B2 | 10/2015 | Reidt et al. | |
| 9,192,164 B2 | 11/2015 | Berentsveig et al. | |
| 9,213,043 B2 | 12/2015 | Cook et al. | |
| 9,222,665 B2 | 12/2015 | Halas et al. | |
| 9,241,491 B2 | 1/2016 | Berentsveig et al. | |
| 9,522,205 B2 | 12/2016 | Ahiska | |
| 9,545,458 B2 | 1/2017 | Halas et al. | |
| 9,616,426 B2 | 4/2017 | Dulaff | |
| 9,625,465 B2 | 4/2017 | Cook et al. | |
| 9,686,824 B2 | 6/2017 | Weston et al. | |
| 9,901,651 B2 | 2/2018 | Finke et al. | |
| 9,950,824 B2 | 4/2018 | Miyahara et al. | |
| 9,974,872 B2 | 5/2018 | Weston et al. | |
| 11,065,352 B2 | 7/2021 | Fritchie et al. | |
| 11,452,787 B2 | 9/2022 | Weston et al. | |
| 2003/0170686 A1 | 9/2003 | Hoet | |
| 2004/0022665 A1 | 2/2004 | Lu | |
| 2007/0026442 A1 | 2/2007 | Calasso et al. | |
| 2009/0291018 A1 | 11/2009 | Wallace et al. | |
| 2010/0198220 A1 | 8/2010 | Boudreaux et al. | |
| 2010/0282739 A1 | 11/2010 | Wallace et al. | |
| 2011/0117202 A1 | 5/2011 | Bourke, Jr. et al. | |
| 2011/0139189 A1 | 6/2011 | Reidt et al. | |
| 2011/0211989 A1 | 9/2011 | Hemphill et al. | |
| 2011/0222889 A1 | 9/2011 | Tabuchi | |
| 2012/0019316 A1 | 1/2012 | Hattersley et al. | |
| 2012/0156102 A1 | 6/2012 | Halas et al. | |
| 2012/0251386 A1 | 10/2012 | Wootton et al. | |
| 2013/0167872 A1 | 7/2013 | Weston et al. | |
| 2014/0037495 A1 | 2/2014 | Ahiska et al. | |
| 2014/0119985 A1 | 5/2014 | Berg et al. | |
| 2014/0119986 A1 | 5/2014 | Finke et al. | |
| 2014/0158678 A1 | 6/2014 | Thomann et al. | |
| 2014/0183178 A1 | 7/2014 | Guichard et al. | |
| 2015/0073352 A1 | 3/2015 | Finke et al. | |
| 2015/0073353 A1 | 3/2015 | Strader | |
| 2015/0224503 A1 | 8/2015 | Dulaff | |
| 2015/0266024 A1 | 9/2015 | Leland | |
| 2015/0296571 A1 | 10/2015 | Holcomb | |
| 2015/0312968 A1 | 10/2015 | Weston et al. | |
| 2017/0246328 A1 | 8/2017 | Weston et al. | |
| 2018/0193498 A1 | 7/2018 | Fritchie et al. | |
| 2018/0264149 A1 | 9/2018 | Weston et al. | |

FOREIGN PATENT DOCUMENTS

| | | |
|---|---|---|
| CN | 2704368 | 6/2005 |
| CN | 1668143 A | 9/2005 |
| CN | 1802044 A | 7/2006 |
| CN | 1986012 A | 6/2007 |
| CN | 101389280 A | 3/2009 |
| CN | 102193447 A | 9/2011 |
| DE | 2911565 A1 | 9/1980 |
| DE | 4428228 A1 | 2/1996 |
| EP | 0121980 A2 | 10/1984 |
| EP | 0727228 A1 | 8/1996 |
| EP | 3101779 | 12/2016 |
| FR | 2730638 A1 | 8/1996 |
| JP | S60143587 | 7/1985 |
| JP | H07201460 A | 8/1995 |
| JP | H11162623 A | 6/1999 |
| JP | 3704425 B2 | 10/2005 |
| JP | 2007078825 A | 3/2007 |
| JP | 2008119417 A | 5/2008 |
| JP | 2009158394 A | 7/2009 |
| JP | 2010246509 A | 11/2010 |
| JP | 2015065091 | 4/2015 |
| WO | 9013318 A1 | 11/1990 |
| WO | 03049530 A2 | 6/2003 |
| WO | 2006006946 | 1/2006 |

(56) References Cited

FOREIGN PATENT DOCUMENTS

| WO | 2006121838 A2 | 11/2006 |
|---|---|---|
| WO | 2011089900 A1 | 7/2011 |
| WO | 2012040868 A2 | 4/2012 |
| WO | 2014035804 A1 | 3/2014 |

OTHER PUBLICATIONS

International Searching Authority, "Invitation to Pay Additional Fees and Partial International Search," issued in connection with corresponding PCT application No. PCT/US2012/070807, dated Apr. 18, 2013, 8 pages.

International Searching Authority, "International Search Report and Written Opinion of the International Searching Authority," issued in connection with application No. PCT/US2012/070807, dated Aug. 30, 2013, 20 pages.

International Bureau, "International Preliminary Report on Patentability," issued in connection with application No. PCT/US2012/070807, dated Jul. 10, 2014, 14 pages.

European Patent Office, "Extended European Search Report," issued in connection with European Patent Application No. 17160886.2, dated Aug. 3, 2017, 8 pages.

European Patent Office, "Communication Under Article 71(3) EPC," issued in connection with European Patent Application No. 12813208.1, dated May 25, 2016, 43 pages.

State Intellectual Property Office of China, "Second Office Action," issued in connection with Chinese Patent Application No. 201280070734.6, dated Aug. 31, 2016, 10 pages.

European Patent Office, "Invitation pursuant to Rule 137(4)," issued in connection with European Patent Application No. 12813208.1, dated Oct. 27, 2016, 3 pages.

European Patent Office, "Invitation Pursuant to Rule 137(4) EPC", issued in connection with European Patent Application No. 12813208.1 dated Aug. 25, 2015, 2 pages.

State Intellectual Property Office of China, "Notification to Grant Patent Right for Invention," issued in connection with application No. 201280070734.6, dated Mar. 3, 2017, 4 pages (includes English translation).

State Intellectual Property Office of China, "Notification of First Office Action and Search Report," issued in connection with Chinese Patent Application No. 201280070734.6, dated Nov. 2, 2015, 15 pages.

United States Patent and Trademark Office, "Office Action", issued in connection with U.S. Appl. No. 13/721,931, dated Jun. 2, 2014, 9 pages.

United States Patent and Trademark Office, "Office Action", issued in connection with U.S. Appl. No. 13/721,931, dated Sep. 11, 2014, 26 pages.

United States Patent and Trademark Office, "Notice of Allowance", issued in connection with U.S. Appl. No. 13/721,931, dated Mar. 4, 2015, 9 pages.

United States Patent and Trademark Office, "Notice of Allowance," issued in connection with U.S. Appl. No. 14/791,964, dated Feb. 14, 2017, 26 pages.

United States Patent and Trademark Office, "Non-final Office Action," issued in connection with U.S. Appl. No. 14/791,964, dated Jun. 17, 2016, 29 pages.

United States Patent and Trademark Office, "Corrected Notice of Allowability," issued in connection with U.S. Appl. No. 14/791,964, dated May 23, 2017, 7 pages.

United States Patent and Trademark Office, "Office Action," issued in connection with U.S. Appl. No. 15/593,955, dated Jul. 3, 2017, 8 pages.

United States Patent and Trademark Office, "Notice of Allowance," issued in connection with U.S. Appl. No. 15/593,955, dated Jan. 22, 2018, 34 pages.

The International Bureau, "International Preliminary Report on Patentability," issued in connection with application No. PCT/US2017/067890, dated Jun. 25, 2019, 10 pages.

International Searching Authority, "International Search Report," issued in connection with International Application No. PCT/US2017/067890, dated Apr. 25, 2018, 16 pages.

United States Patent and Trademark Office, "Final Office Action", issued in connection with U.S. Appl. No. 15/984,741, dated Jun. 25, 2020, 9 pages.

National Intellectual Property Administration, P.R. China, "First Office Action," issued in connection with Chinese Patent Application No. 201710352255.8, dated Jan. 15, 2020, 17 pages (includes English translation).

United States Patent and Trademark Office, "Non-Final Office Action," issued in connection with U.S. Appl. No. 15/984,741, dated Mar. 5, 2020, 8 pages.

Chinese Patent Office, "Second Office Action," issued in connection with Chinese Patent Application No. 201710352255.8, dated Jul. 24, 2020, 7 pages (includes English translation).

United States Patent and Trademark Office, "Final Office Action," issued in connection with U.S. Appl. No. 15/984,741 dated Oct. 7, 2020, 12 pages.

Japanese Patent Office, "Office Action," issued in connection with Japanese Patent Application No. 2019-534265, dated Sep. 8, 2020, 8 pages (includes English translation).

Chinese Patent Office, "Notification to Grant Patent Right for Invention," issued in connection with Chinese Patent Application No. 201710352255.8, dated Nov. 5, 2020, 4 pages (includes English translation).

United States Patent and Trademark Office, "Advisory Action," issued in connection with U.S. Appl. No. 15/984,741 dated Dec. 24, 2020, 3 pages.

European Patent Office, "Communication Pursuant to Article 94(3) EPC," issued in connection with European Patent Application No. 17842406.5, dated Mar. 24, 2021, 5 pages.

The State Intellectual Property Office of Peoples Republic of China, "First Office Action," issued in connection with Chinese Patent Application No. 201780087034, dated Mar. 5, 2021, 34 pages (includes English translation).

European Patent Office, "Communication Pursuant to Article 94(3) EPC," issued in connection with European Patent Application No. 17160886.2, dated May 18, 2021, 4 pages.

Japanese Patent Office, "Final Decision to Allowance," issued in connection with Japanese Patent Application No. 2019-534265, dated Apr. 27, 2021, 4 pages (includes English translation).

United States Patent and Trademark Office, "Non-Final Office Action," issued in connection with U.S. Appl. No. 15/851,199, dated Apr. 6, 2020, 10 pages.

United States Patent and Trademark Office, "Restriction," issued in connection with U.S. Appl. No. 15/851,199, dated Jan. 10, 2020, 6 pages.

United States Patent and Trademark Office, "Final Office Action," issued in connection with U.S. Appl. No. 15/851,199 on Nov. 17, 2020, 13 pages.

United States Patent and Trademark Office, "Notice of Allowance," issued in connection with U.S. Appl. No. 15/851,199, dated on Mar. 17, 2021, 8 pages.

United States Patent and Trademark Office, "Corrected Notice of Allowance," issued in connection with U.S. Appl. No. 15/851,199, dated May 18, 2021, 2 pages.

United States Patent and Trademark Office, "Supplemental Notice of Allowance," issued in connection with U.S. Appl. No. 15/851,199, dated May 27, 2021, 2 pages.

United States Patent and Trademark Office, "Supplemental Notice of Allowance," issued in connection with U.S. Appl. No. 15/851,199, dated on Jun. 24, 2021, 2 pages.

United States Patent and Trademark Office, "Non-Final Office Action," issued in connection with U.S. Appl. No. 15/984,741, dated Jul. 20, 2021, 18 pages,.

European Patent Office, "Intention to Grant," issued in connection with European Patent Application No. 12813208.1, dated Aug. 6, 2021, 8 pages.

United States Patent and Trademark Office, "Notice of Allowance," issued in connection with U.S. Appl. No. 15/984,741, dated Dec. 15, 2021, 8 pages.

(56) References Cited

OTHER PUBLICATIONS

National Intellectual Property Administration, P.R. China, "Notification to Grant Patent Right for Invention," issued in connection with Chinese Patent No. 201780087034.0, dated Mar. 23, 2022, 4 pages (includes English translation).
United States Patent and Trademark Office, "Notice of Allowance and Fee(s) Due," issued in connection with U.S. Appl. No. 15/984,741, dated Mar. 30, 2022, 6 pages.
United States Patent and Trademark Office, "Corrected Notice of Allowability," issued in connection with U.S. Appl. No. 15/984,741, dated May 11, 2022, 3 pages.
Chinese Patent Office, "First Office Action," issued in connection with Chinese Patent Application No. 202110075918.2, dated Apr. 28, 2022, 11 pages (included English translation).
United States Patent and Trademark Office, "Corrected Notice of Allowability," issued in connection with U.S. Appl. No. 15/984,741, dated Jul. 7, 2022, 3 pages.
European Patent Office, "Communication pursuant to Article 94(3) EPC," issued in connection with European Patent Application No. 17842406.5, dated Jun. 9, 2022, 5 pages.
Japanese Patent Office, "Office Action," issued in connection with Japanese Patent Application No. 2021-113291, dated Jul. 12, 2022, 9 pages (English translation provided).
United States Patent and Trademark Office, "Corrected Notice of Allowability," issued in connection with U.S. Appl. No. 15/984,741, dated Aug. 17, 2022, 3 pages.
European Patent Office, "Communication pursuant to Article 94(3) EPC," issued in connection with European Patent Application No. 17160886.2, dated Oct. 10, 2022, 4 pages.
Japanese Patent Office, "Decision to Grant a Patent," issued in connection with Japanese Patent Application No. 2021-113291, dated Nov. 25, 2022, 5 pages. (English translation included).
National Intellectual Property Administration, P.R. China, "Notification to Grant Patent Right for Invention," issued in connection with Chinese Patent Application No. 202110075918.2, dated Nov. 30, 2022, (English translation included).
European Patent Office, "Communication pursuant to Article 94(3) EPC," issued in connection with European Patent Application No. 17160886.2, dated Apr. 25, 4 pages.
United States Patent and Trademark Office, "Advisory Action," issued in connection with U.S. Appl. No. 15/984,741, mailed on Sep. 3, 2020, 3 pages.
European Patent Office, "Summons to Attend Oral Proceedings Pursuant to Rule 115(1) EPC," issued in connection with European Patent Application No. 17160886.2, dated Nov. 27, 2023, 6 pages.
European Patent Office, "Communication Pursuant to Article 94(3) EPC," issued in connection with European Patent Application No. 17842406.5, dated Nov. 29, 2023, 5 pages.
The State Intellectual Property Office of People's Republic of China, "First Office Action and First Search," issued in connection with Chinese Patent Application No. 202310125668.8, dated Jul. 25, 2024, 14 pages. [English Translation Included].
The State Intellectual Property Office of People's Republic of China, "First Office Action and First Search," issued in connection with Application No. 202210633653.8, dated Jul. 15, 2024, 20 pages. [English Translation Included].
Japan Patent Office "Design of Refusal", issued in connection with Japanese Patent Application No. 2022-201866, dated Aug. 6, 2024, 13 pages. [English Translation Included].

\* cited by examiner

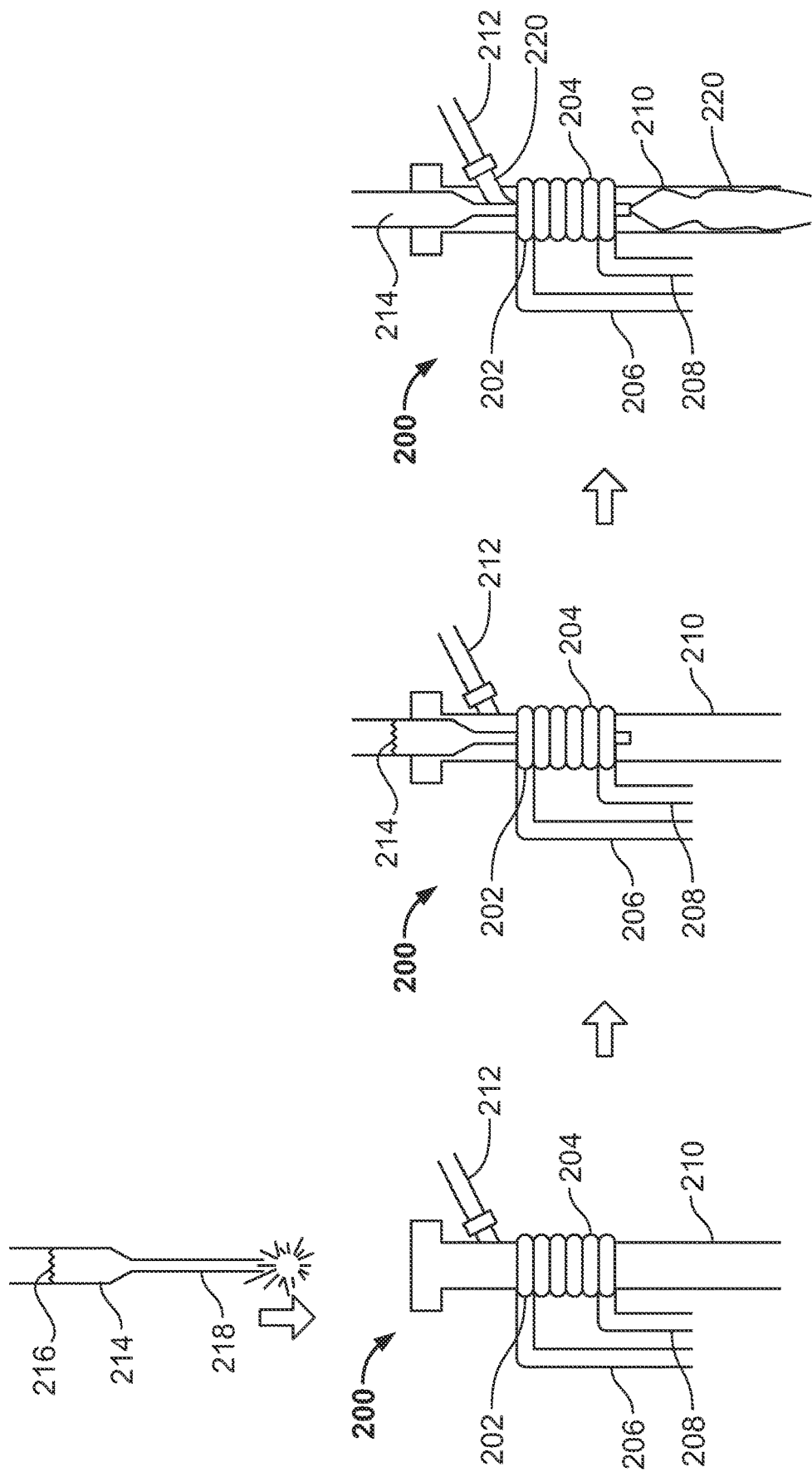

METHODS AND APPARATUS TO REDUCE BIOLOGICAL CARRYOVER USING INDUCTION HEATING

RELATED APPLICATIONS

This patent claims priority to U.S. patent application Ser. No. 15/984,741, now U.S. Pat. No. 11,452,787, titled "Methods and Apparatus to Reduce Biological Carryover Using Induction Heating" and filed May 21, 2018. U.S. patent application Ser. No. 15/984,741 claims priority to U.S. patent application Ser. No. 15/593,955, now U.S. Pat. No. 9,974,872, titled "Methods and Apparatus to Reduce Biological Carryover Using Induction Heating" and filed May 12, 2017. U.S. patent application Ser. No. 15/593,955 claims priority to U.S. patent application Ser. No. 14/791,964, now U.S. Pat. No. 9,686,824, titled "Methods and Apparatus to Reduce Biological Carryover Using Induction Heating" and filed on Jul. 6, 2015. U.S. patent application Ser. No. 14/791,964 claims priority to U.S. patent application Ser. No. 13/721,931, now U.S. Pat. No. 9,073,094, titled "Methods and Apparatus to Reduce Biological Carryover Using Induction Heating" and filed on Dec. 20, 2012. U.S. patent application Ser. No. 13/721,931 claims priority to U.S. Provisional Patent Application No. 61/580,913, titled "Methods and Apparatus to Reduce Biological Carryover Using Induction Heating" and filed on Dec. 28, 2011. U.S. patent application Ser. No. 15/984,741, U.S. patent application Ser. No. 15/593,955, U.S. patent application Ser. No. 14/791,964, U.S. patent application Ser. No. 13/721,931, and U.S. Provisional Patent Application No. 61/580,913 are incorporated herein by reference in their entireties.

FIELD OF THE DISCLOSURE

This disclosure relates generally to medical diagnostic equipment and, more particularly, to methods and apparatus to reduce biological carryover using induction heating.

BACKGROUND

Probes are used in medical diagnostic equipment to aspirate and/or dispense samples and reagents into/from sample tubes and reaction vessels. The probability of biological carryover or cross contamination is increased when probes are reused. Some existing methods for preventing cross contamination of proteins require probes to be replaced. Probe replacement produces significant waste and increases operation costs and time.

BRIEF DESCRIPTION OF THE DRAWINGS

FIGS. 2A-C illustrate an example aspiration and dispense device being inductively heated and washed.

DETAILED DESCRIPTION

Figure 1:
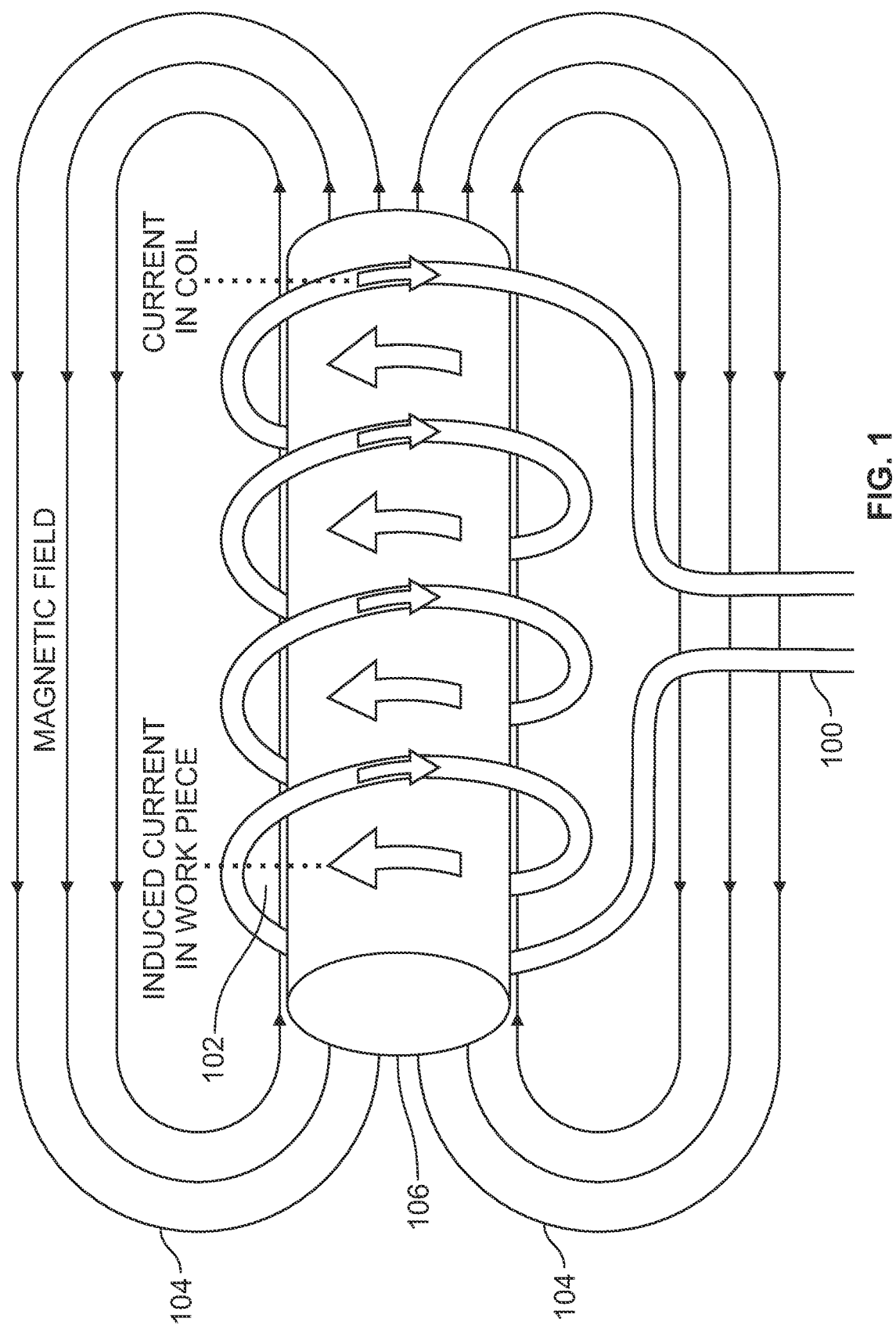
FIG. 1 is a schematic illustration of electromagnetic induction.

Automated medical diagnostic equipment and automated pipette systems use one or more aspiration and/or dispense devices such as, for example pipettes or probes, to aspirate and/or dispense samples such as biological samples and/or reagents into and/or from reaction vessels such as, for example, one or more well(s) on a multi-well plate. The exterior and interior surfaces of the aspiration and/or dispense device come into contact with the sample and/or reagent and a portion of the sample and/or reagent may remain on the exterior and/or interior surface after the sample and/or reagent has been dispensed. Subsequent use of the aspiration and/or dispense device could result in sample carryover or reagent carryover. Such carryover is the transfer of the residual sample and/or reagent to another sample and/or reagent, which contaminates the sample and/or reagent and may lead to an inaccurate analysis or diagnosis.

Some systems include a wash station to wash the surfaces of an aspiration and/or dispense device. However, wash stations require volumes of wash solution. In addition, any defects, scratches, indentations or other imperfections or irregularities of the surfaces of the aspiration and/or dispense device may harbor biological samples and/or reagents such that the aspiration and/or dispense device is not sufficiently clean after a washing cycle.

In other systems, electrostatic induction is used to heat an aspiration and/or dispense device to a level of sterilization. Such systems create a non-alternating electrical potential (e.g., a voltage) across the aspiration and/or dispense device and create heat via electrical resistance. These systems require a relatively high voltage and current and, therefore, have an increased risk of electrical shorting. In addition, these systems typically heat the entire aspiration and/or dispense device and, therefore, localized heating and cleaning of only a contaminated region is not possible. Furthermore, the current flows in a non-uniform manner through the aspiration and/or dispense device along the paths of least resistance. Areas of the surface of the aspiration and/or dispense device that include defects, scratches, dents or other irregularities have higher resistance. Therefore, these areas, which are particularly sensitive to biological buildup, experience less current flow and, therefore, less heating than other areas of the aspiration and/or dispense device. Thus, devices cleaned through electrostatic induction may not be sufficiently free from biological carryover.

The example systems, methods and apparatus disclosed herein use electromagnetic induction heating to clean aspiration and/or dispense devices. In the examples disclosed herein, reactive proteins and/or other biological entities on the surfaces of the aspiration and/or dispense device are deactivated and/or denatured using heat that is generated via electromagnetic induction. The deactivation or denaturing of the biological substances provides protection against biological carryover by reducing or eliminating cross contamination between discrete reactions.

The inductive heating is achieved through a metallic coil, or any other shape of continuous electrically conducting media in which the size and shape and is designed to provide a desired heating pattern, through which a high frequency, high current electrical signal flows to induce an opposing current in a target object (e.g., the aspiration and/or dispense device to be cleaned) per Faraday's law of induction. The opposing current heats the aspiration and/or dispense device and the residual proteins and/or other biological matter fixed thereto. The proteins and/or other biological matter are heated above a critical temperature to change the manner in which these materials react and bind to other objects or substances, which reduces the chance for unintended reactions. The examples disclosed herein reduce or eliminate the likelihood of contamination between discrete fluid movements or reactions, without the need for extensive washing, expensive coatings or single use probes.

An example method disclosed herein includes generating an alternating electromagnetic field and introducing an aspiration and/or dispense device into the electromagnetic field. The example method also includes inductively heating the aspiration and/or dispense device with the electromagnetic field to at least one of denature or deactivate at least one of a protein or a biological entity on a surface of the aspiration and/or dispense device.

Some examples disclosed herein include washing the aspiration and/or dispense device prior to introducing the aspiration and/or dispense device into the electromagnetic field. In addition, some examples include washing the aspiration and/or dispense device after inductively heating the aspiration and/or dispense device with the electromagnetic field. In some examples, the washing comprises washing with a cooling wash to lower a temperature of the aspiration and/or dispense device. Also, some examples include washing the aspiration and dispense device during inductively heating the aspiration and dispense device with the electromagnetic field.

Some examples disclosed herein include generating the electromagnetic field by flowing a current through an electrically conducting media, using a frequency that is based on a diameter of the aspiration and/or dispense device. Also, some examples disclosed herein include generating the electromagnetic field by flowing a current through an electrically conducting media, using a frequency that is based on a thickness of a skin or wall of the aspiration and/or dispense device. In some examples, the electrically conducting media comprises a coil. In other examples, the electrically conducting media comprises any other shape of continuous electrically conducting media in which the size and shape and is designed to provide a desired heating pattern.

In some of the disclosed examples, the aspiration and/or dispense device is raised and/or lowered through the electromagnetic field to inductively heat the aspiration and/or dispense device along a length of the aspiration and/or dispense device. Also, in some examples, the thickness of the skin varies along the length of the aspiration and/or dispense device, and the frequency is adjusted as the aspiration and/or dispense device is raised or lowered.

In some examples disclosed herein, only a portion of the aspiration and/or dispense device is inductively heated. In other examples, inductively heating the aspiration and/or dispense device with the electromagnetic field includes heating the aspiration and/or dispense device without directly contacting the aspiration and dispense device via an electrical and/or an electrostatic connection.

In some examples, generating the alternating electromagnetic field comprises using a standard electrical wall outlet. Also, some of the disclosed examples include disposing a wash cup between the aspiration and/or dispense device and an electrically conducting media such as, for example, a coil used to create the electromagnetic field and preventing direct contact between the aspiration and dispense device and the electrically conducting media with the wash cup.

An example system disclosed herein includes an electromagnetic field generator and an aspiration and/or dispense device to be introduced into the electromagnetic field and to be inductively heated with the electromagnetic field. The example system also includes a wash cup to interpose the electromagnetic field generator and the aspiration and dispense device to prevent direct contact therebetween. In some example systems, the aspiration and dispense device lacks an electrical connector coupled to a surface of the aspiration and dispense device, and the aspiration and dispense device is electrically isolated.

Some example systems also include a washer to wash the aspiration and/or dispense device prior to introducing the aspiration and/or dispense device into the electromagnetic field and/or after inductively heating the aspiration and/or dispense device with the electromagnetic field. In some examples, the washer is to wash with a cooling wash to lower a temperature of the aspiration and/or dispense device.

In some examples, the electromagnetic field generator comprises a frequency generator and a coil, and the frequency generator is to generate a variable frequency current to flow through the coil. The frequency is based on a diameter of the aspiration and/or dispense device. Also, in some examples, the electromagnetic field generator comprises a frequency generator and an electrically conducting media (e.g., a coil or any other shape of continuous electrically conducting media in which the size and shape and is designed to provide a desired heating pattern), and the frequency generator to generate a variable frequency current to flow through the electrically conducting media. The frequency is based on a thickness of a skin of the aspiration and/or dispense device.

Some example systems include an arm to raise or lower the aspiration and dispense device through the electromagnetic field to inductively heat the aspiration and/or dispense device along a length of the aspiration and dispense device. Some example systems include a frequency generator to adjust the frequency as the aspiration and/or dispense device is raised or lowered. Such frequency may be adjusted where the thickness of the skin varies along the length of the aspiration and/or dispense device.

In some examples, the electromagnetic field is to inductively heat only a portion of the aspiration and/or dispense device. In some examples, the aspiration and/or dispense device is to be heated without directly contacting an electrical connection. In some example systems disclosed herein, a surface of the aspiration and/or dispense device is heated to denature or deactivate at least one of a protein or a biological entity on the surface.

Some example systems include a controller and a feedback loop. The feedback loop is to provide data to the controller comprising one or more of frequency, an impedance, a presence of the aspiration and dispense device in the electromagnetic field, a voltage reading or a current reading and the controller to change the frequency to change a strength of the electromagnetic field to vary a heating temperature of the aspiration and/or dispense device based on the data.

Also disclosed are example tangible machine readable media having instructions stored thereon which, when executed, cause a machine to generate an alternating electromagnetic field and introduce an aspiration and/or dispense device into the electromagnetic field. The example instructions further cause the machine to inductively heat the aspiration and/or dispense device with the electromagnetic field to denature and/or deactivate at least one of a protein or a biological entity on a surface of the aspiration and/or dispense device.

Turning now to the figures, FIG. 1 shows a schematic illustration of electromagnetic induction. As shown in FIG. 1, a coil 100 includes a high frequency alternating (AC) current flowing in a first direction as represented by the white arrows. The interior of the loops of the coil 100 form a work space 102. When the current is flowing through the coil 100, an alternating magnetic field 104 extends through the workspace 102 and around the coil 100. A work piece 106, which may represent for example, a portion of a probe or other aspiration and/or dispense device, may be inserted into the workspace 102. The alternating magnetic field 104 produces eddy currents in the work piece 106. The eddy currents flow in a direction opposite the alternating current in the coil 100, as represented by the larger arrows. Magnetic hysteresis losses and Ohmic heating raise the temperature of the work piece 106. The heat changes the binding properties of any proteins or other biological entities that may be present on surfaces of the work piece 106 to denature and deactivate such proteins and biological entities. The foregoing process works with ferrous metals, non-magnetic metals, and/or other conductive materials.

FIGS. 2A-C illustrate a portion of an example system 200 to reduce biological carryover during three operations. The example system 200 includes an electromagnetic field generator 202 which, in this example, includes a metal coil 204 such as, for example, a copper coil. The coil 204 has a first lead 206 and a second lead 208 to electrically couple the coil 204 to a power source such as, for example, an AC power source. The interior of the coil 204 forms a workspace into which one or more work piece(s) may be disposed, as described below. As described in connection with FIG. 1, when an electrical current flows through the coil 204, a magnetic field is created and an opposing current is induced in the work piece(s).

The example system 200 also includes an example wash cup 210. In this example, the wash cup 210 is an open-ended splash container that may be made of, for example, glass, ceramic, plastic, electrically insulating and/or any other suitable non-metallic material. The wash cup 210 includes an inlet 212 to enable the introduction of wash fluid into the wash cup 210. The system 200 also includes a pipettor probe or other aspiration and/or dispense device 214. In this example, the aspiration and/or dispense device 214 is a metal probe such as, for example, stainless steel. In FIG. 2A, the aspiration and/or dispense device 214 is above or outside of the coil 204. The aspiration and/or dispense device 214 includes a liquid 216, which may be, for example, a sample, a reagent a wash solution or any combination thereof. In this example, an exterior surface of the aspiration and/or dispense device 214 is contaminated with protein or biological matter 218. The protein or biological matter 218 may be adhered to the exterior surface in a scratch or other surface anomaly and/or due to hydrophobicity, ionic charges, electrostatic charges, protein adsorption, and/or surface energy.

In FIG. 2B, the aspiration and/or dispense device 214 is lowered into the wash cup 210, and the coil 204 is powered to generate an alternating electromagnetic field. In this example, the wash cup 210 interposes the aspiration and/or dispense device 214 to prevent direct contact therebetween. Thus, the aspiration and/or dispense device 214 is remotely inductively heated preventing biological contamination with the coil 204. An advantage to this structure is that a standard aspiration and/or dispense device (e.g., probe) can be used.

There is no need for an electrical connector fitted to the aspiration and/or dispense device. Thus, the aspiration and/or dispense device is electrically isolated. The electrical isolation reduces the chances of an operator experiencing an electrical shock because of accidental (or intentional) contact with the aspiration and/or dispense device. The current generated in the aspiration and/or dispense device occurs only where there is a strong alternating magnetic field, and that current is generated only in the material of the aspiration and/or dispense device. More specifically, an operator does not provide a grounding path for the current being generated in the work piece (e.g., the aspiration and/or dispense device) because the current is only being generated within the immediate magnetic field, and the current is in self-contained and isolated loops.

The electrical current in the coil 204 creates a magnetic field that induces an electrical current in the aspiration and/or dispense device 214. The electrical current in the aspiration and/or dispense device 214 generates heat such that the aspiration and/or dispense device 214 is inductively heated. In this example, the aspiration and/or dispense device 214 may be heated to a temperature of, for example 300° C., and any residual proteins and/or biological matter are coagulated, denatured and deactivated. Temperatures as low as, for example, 43° C. denature some proteins. Most proteins incinerate by 300° C. The temperature may be raised much higher, including, for example, 760° C. If there are scratches or other surface anomalies on the aspiration and/or dispense device 214, the current is diverted around the root of the imperfection, which increases the local current density and therefore the local heat generation and ensures cleaning of these areas. When there is a crack, scratch, or imperfection, the current is concentrated and directed under the crack, scratch, or imperfection such that the base experiences increased heating, which is where contamination may accumulate. The liquid 216 may be dispensed from the aspiration and/or dispense device 214 prior to or during this operation.

In addition, in the disclosed example, the electromagnetic field inductively heats only a portion of the aspiration and/or dispense device 214 to increase target cleaning of the aspiration and/or dispense device 214 and eliminates the need to heat the entire aspiration and/or dispense device 214. For example, only the portion of the aspiration and/or dispense device 214 located within the work space defined by the coil 204 is heated. Some example systems include an arm (see FIG. 6) to raise or lower the aspiration and/or dispense device 214 through the electromagnetic field to inductively heat different portions of the aspiration and/or dispense device 214 along a length of the aspiration and/or dispense device 214.

Also, as described in greater detail below, in some examples, the current flowing through the coil 204 is varied depending on a diameter of the portion of the aspiration and/or dispense device 214 in the work space and/or depending on a thickness of a skin of the portion of the aspiration and/or dispense device 214 in the work space. In some examples, the thickness of the skin and/or the diameter varies along the length of the aspiration and/or dispense device 214 and a frequency of the current is adjusted as the aspiration and/or dispense device 214 is raised or lowered.

In some examples, there is a pre-treatment procedure such as, for example, a prewash to clean the surfaces of the aspiration and/or dispense device 214 prior to the entry of the aspiration and/or dispense device 214 into the work space of the coil 204. Also, in some examples, there is a post-treatment procedure such as, for example, a postwash as shown in FIG. 2C. In this example, the power to the coil 204 is deactivated and an active probe wash flushes wash fluid 220 through the inlet 212 to wash the outer surface of the aspiration and/or dispense device 214 to remove residue proteins and/or other biological materials. The wash fluid 220 has a relatively cooler temperature to reduce the temperature of the aspiration and/or dispense device 214 to return the temperature of the aspiration and/or dispense device to, for example, ambient temperature. The aspiration and/or dispense device 214 is ready to be reused following the operation of FIG. 2B and/or FIG. 2C.

Figure 3E:
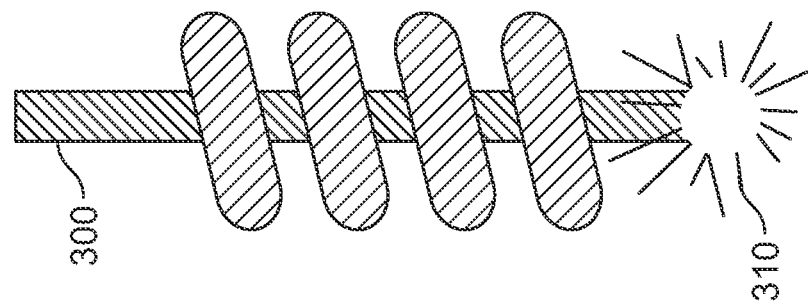
FIGS. 3A-E illustrate another example aspiration and dispense device being inductively heated and washed.
Figure 3D:
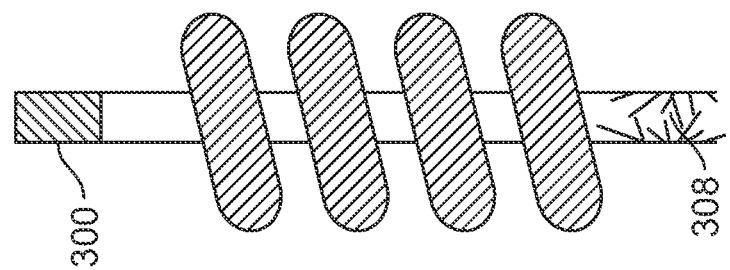
Figure 3C:
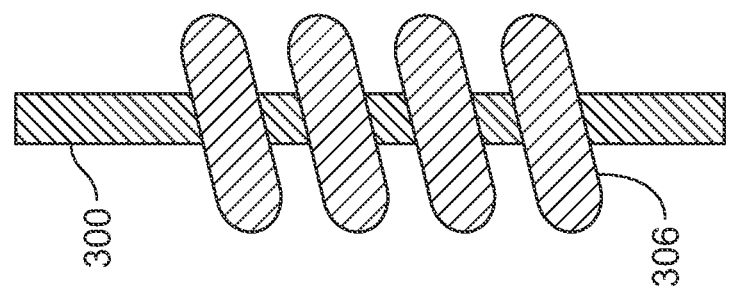
Figure 3B:
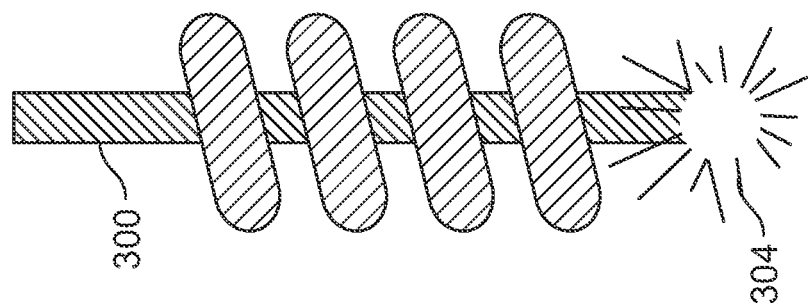
Figure 3A:
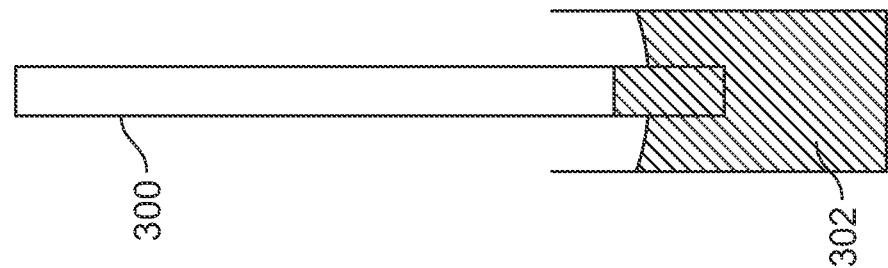

FIGS. 3A-E illustrate another example aspiration and/or dispense device 300 being inductively heated and washed. The aspiration and/or dispense device 300 is used to transport a sample or reagent 302 (FIG. 3A). The exterior and interior surfaces of the aspiration and/or dispense device 300 include contaminants 304 (FIG. 3B). In some examples, the aspiration and/or dispense device 300 is washed to remove the contaminants 304, and the aspiration and/or dispense device 300 is placed in the center of a coil 306 (FIG. 3C). The interior of the aspiration and/or dispense device 300 may also be cleared, but residual contaminants 308 may remain (FIG. 3D). Though FIGS. 3B-D shows the aspiration and/or dispense device 300 in the coil 306 during the pre-wash steps and the aspiration/dispense to clear the device 300, these processes or operations may occur prior to insertion of the aspiration and/or dispense device 300 in the coil 306.

An alternating current is passed through the coil 306 (FIG. 3D), which creates a magnetic field that induces eddy currents in the aspiration and/or dispense device 300. The eddy currents generate heat, as disclosed above to denature and deactivate any contaminants on and/or in the aspiration and/or dispense device 300. In some examples a post-wash treatment is provided to remove carbonized proteins 310 (FIG. 3E) or otherwise deactivated and/or unbound proteins 310 that may reside in the fluid channel and/or to cool the aspiration and/or dispense device 300.

Figure 4:
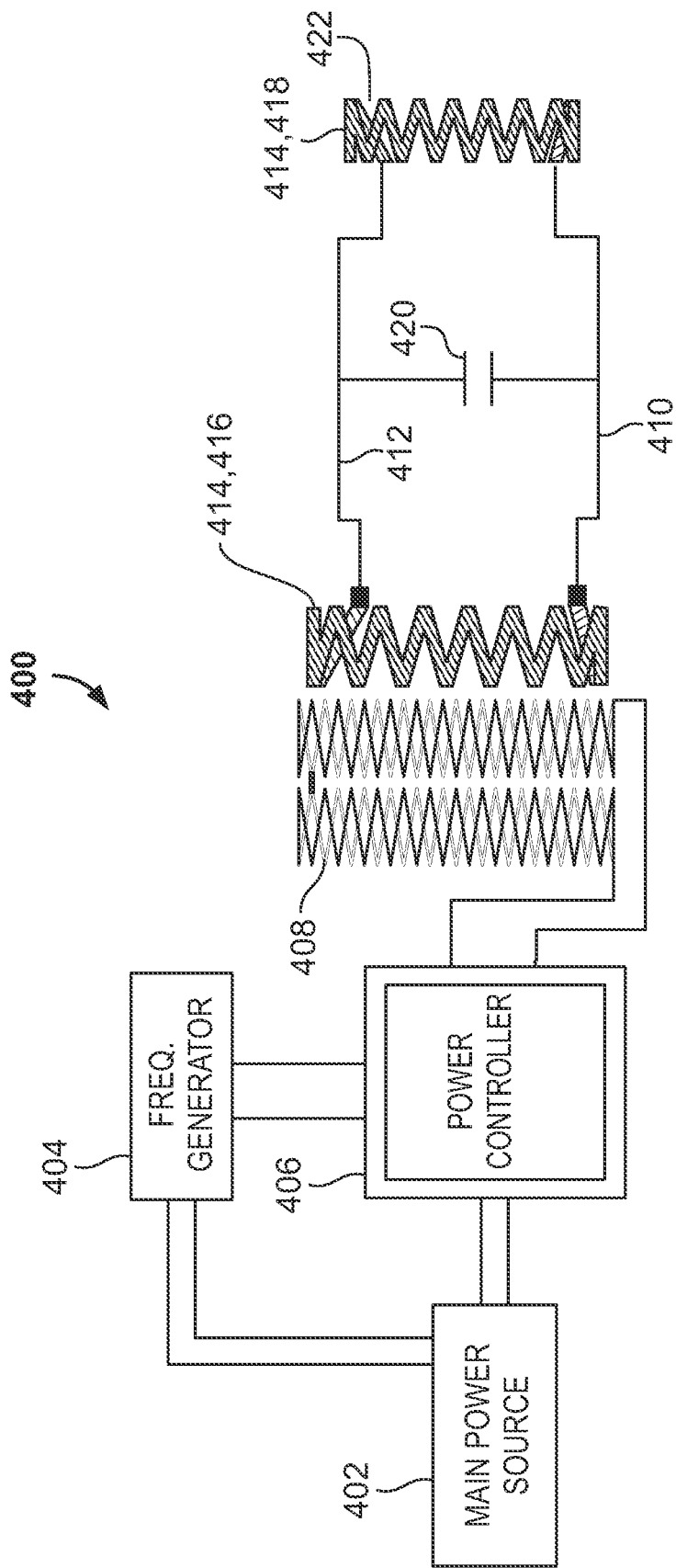
FIG. 4 is a schematic illustration of an example architecture for an electromagnetic field generator.

FIG. 4 illustrates an example circuit architecture for an electromagnetic field generator 400 that may be included, for example, in a medical diagnostic system or laboratory automation equipment like an automated pipetting system. The example includes a main power source 402. In this example, the main power source 402 is the same power source for the entire medical diagnostic system. Thus, the main power source 402 is the same line voltage and frequency as used by the rest of the system and as received from a standard wall-mounted electrical outlet. Thus, in this example, there is no dedicated line or high voltage source used to power the electromagnetic field generator 400. Instead, the main power is a low current, high voltage power. The example generator 400 includes a frequency generator 404 that generates the frequency needed to operate the generator 400. In this example, the frequency may be, for example about 637 kHz. The frequency is adjustable and can be varied based on the characteristics of an aspiration and/or dispense device or other work piece to be placed in the magnetic field and heated.

In some examples, the frequency also is adjustable based on the type of reagent and/or sample including, for example, whether the contents of the aspiration and/or dispense device was previously a blood sample or will be a blood sample in a future use. For example, the frequency may be adjusted based on the amount of bound proteins that is expected for a particular type of sample. Thus, for example, the frequency/power could be reduced for "cleaner solutions" (i.e., solutions with an expectation of a lower amount of bound proteins or other biological carryover). The sample itself does not impact the rate of or generation of heat in the aspiration and/or dispense device.

In addition, the frequency may also be adjusted if, for example, a future test is particularly sensitive to carryover. In such examples, the frequency may be adjusted to maximize the heat for reducing and/or eliminating carryover. For example, if an assay has a particular sensitivity to carryover then a higher and/or a maximum available power and heat generation may be used to reduce and/or eliminate carryover.

Furthermore, in other examples, the frequency may be adjusted to use the lowest effective heat for a particular heating/cleaning cycle to reduce material stress on the probe, shorten a cycle time and/or maximize energy efficiency. In some examples, power usage and/or frequency is tailored based on an amount of contaminate aspirated. In such examples, a higher power may be used for a cleaning cycle that involves a relatively larger amount of probe length to be cleaned. Also, in some examples, a lower power may be used for cleaning a smaller area. In both of these examples, the time to clean could be consistent even though the power used and the length of the probe cleaned could be different. In addition, in some examples, the time for cleaning and, thus, the time an aspiration and/or dispense device spends heated in the electromagnetic field may be reduced where, for example, a small area of the aspiration and/or dispense device (e.g., probe) is to be cleaned and a relatively higher power is used. In some examples, the aspiration and/or dispense device does not experience a level of heat near a critical temperature at which the material of the aspiration and/or dispense device begins to exhibit heat related issues. In addition, control of the frequency and, thus, the heat level, may be used to reduce the material stress, increase the useful life of the aspiration and/or dispense device and mitigate failure. Also, in some examples, when less power in the induction heater (e.g., in the coil) is desired, the frequency may be increased with relation to the nominal. This causes less strain on semiconductor switches (e.g., in the example systems 400, 500, 600, 700 disclosed herein) when the driving frequency is higher than the resonant frequency because the switches are not "hard switching" against a potential.

The example generator 400 also includes a power controller 406 to control the flow of power from the main power source 402 at the frequency generated by the frequency generator 404. A square wave signal or waveform is used in this example, but other waveforms also may be used including, for example, sinusoidal, triangular or saw tooth waveforms. An example input power may be about 450 Watts.

The example generator 400 also includes a transformer 408. The transformer 408 steps down the voltage and increases the current. The transformer 408 also provides isolation between a resonant or tank circuit 410 and the main power 402. The transformer 408 also provides a means of electrically matching the tank circuit 410 to the main power 402 and power controller 406 by magnifying or reducing the impedance of the tank circuit 410 as seen by the main power 402 and power controller 406 such that excessive current is not drawn by the generator 400. In some examples, the transformer 408 may have a turns ratio of about 5.45:1. Thus, in this example, the current after the transformer 408 is about 5.45 times larger than the current before the transformer 408, and the voltage after the transformer 408 is reduced by 5.45 times.

The tank circuit 410 is a parallel inductance-resistance-capacitance (LRC) circuit comprising a resistor 412 (the resistance of the system including transmission wires and the inherent resistance of the following components), an inductor 414 (the inductance of a both a coil 416 coupled to the transformer 408 and a work coil 418) and a capacitor 420 connected in parallel with a value chosen so that the tank circuit 410 resonates at the frequency of the frequency generator 404. The capacitor 420 provides the capacitance needed for the resonant circuit, and the work coil 418 provides the inductance and at least some of the resistance in the tank circuit 410. In this example, the capacitor 420 is about 0.45 µF in parallel, and the work coil 418 has an inductance of about 1.4 µH. The tank circuit 410 further increases the current for the work coil 418. The example work coil 418 operates as disclosed above to generate an alternating magnetic field which results in an opposing magnetic field generated by the work piece and therefore raises the surface temperature of any work piece disposed within a work space 422 in the interior of the work coil 418. In this example, the pre-transformer current is about 4.4A, the post-transformer current is about 24A. The tank circuit 410, in this example, increases the current further to about 240A, resulting in an overall increase of about 54.5-fold at the work coil 418. Also, the example work coil 418 may raise the surface temperature of a work piece such as an aspiration and/or dispense device 0-100° C. in less than one second, 0-300° C. in one to two seconds, and 700-800° C. within seven seconds.

There are several design considerations for optimizing the operation of the example generator 400 including, for example, coil design and selection (inductance magnitude, resistance value, small gap between the coils and the work piece), the component to be heated (physical dimensions, material composition), the amount of main power available (voltage, current), the desired heating rate, the desired maximum temperature and the type of heating desired (through heating, surface heating). These considerations affect the components used in the example generator 400 including, for example, the nominal frequency generated at the frequency generator 404 (for heating the work piece), the capacitance needed (Farad value and kVAR value), the tank circuit 410 multiplication value (Q), the phase angle of the tank circuit 410 (φ) (unity power factor at cos(φ)=1), the ratio and location of the transformer 408, power source design, and connecting wire selection (to minimize stray induction and voltage drop).

Specifically, the frequency to be used for a particular work piece depends on the desired or physical skin thickness of the work piece, and the thickness depends on the outer diameter of the work piece assuming but not limited to a cylindrical cross-section, the wall thickness and the material composition. The skin thickness is defined as the depth where, for example, about 86% of the induced power is generated. The optimum depth for a tube or cylindrically-shaped work piece is defined by Equation (1) below.

$$3.5 = \frac{t \cdot d}{\delta^2} \quad \text{Eqn. (1)}$$

In Equation (1), the skin thickness is represented by $\delta$, t=wall thickness (m), and d=tube diameter (m). Equation (1) can be solved for the skin thickness, which can be used in Equation (2) below to calculate the frequency, f.

$$\delta = \sqrt{\frac{\rho}{\pi \cdot \mu \cdot f}} \quad \text{Eqn. (2)}$$

In Equation 2, resistivity is represented by $\rho$ (µΩm) and µ represents the magnetic permeability (H/m). Equation (2) can be solved to determine the frequency, f (Hz).

Selection of components for the tank circuit 410 depend on the desired frequency f (Hz), the capacitance C (F), and the inductance L (H) as shown below in Equation (3).

$$f = \frac{1}{2\pi\sqrt{LC}} \quad \text{Eqn. (3)}$$

In addition, the Q factor of the tank circuit 410 may be controlled or manipulated via the kilo-volt ampere reactive (kVAR), power (W), the angular frequency ω (rad/s), the capacitance C (F), the voltage (V), the current I (A), the resistance R (Ω), inductance L (H) and/or the inductive reactance $X_L$ (Ω) as shown below in Equation (4).

$$Q = \frac{kVAr}{kW} = \frac{VAr}{W} = \frac{\omega CV^2}{I^2R} = \frac{\omega L}{R} = \frac{X_L}{R} \quad \text{Eqn. (4)}$$

A higher Q value produces a smaller bandwidth, which is more difficult to tune for resonance but provides a higher current multiplication in the tank circuit 410. Whereas a smaller Q value allows for a larger bandwidth, which is easier to tune for resonance and more resistant to de-tuning but provides a lower current multiplication in the tank circuit 410. After the components for the tank circuit have been selected, the impedance Z (Ω) of the circuit may be calculated and the ratio of the transformer 408 may be selected for correct matching and to not draw excessive current from the main power source 402. The impedance $Z_{eq}$ (Ω) of the tank circuit depends on the angular frequency ω (rad/s), the capacitance C (F), the equivalent series resistance of the capacitor $R_C$ (Ω), the series resistance of the inductor $R_L$ (Ω), inductance L (H), equivalent circuit resistance $R_{eq}$ (Ω), and equivalent circuit impedance $X_{eq}$ (Ω), as shown below in Equations (5), (6) and (7).

$$Z_{eq} = R_{eq} + jX_{eq} = |Z|e^{j\varphi} \quad \text{Eqn. (5)}$$

$$R_{eq} = \frac{\left(R_L R_C + \frac{L}{C}\right)(R_L + R_C) + \left(\omega L R_C - \frac{R_L}{\omega C}\right)\left(\omega L - \frac{1}{\omega C}\right)}{(R_L + R_C)^2 + \left(\omega L - \frac{1}{\omega C}\right)^2} \quad \text{Eqn. (6)}$$

$$X_{eq} = \frac{\left(\omega L R_C - \frac{R_L}{\omega C}\right)(R_L + R_C) - \left(R_L R_C + \frac{L}{C}\right)\left(\omega L - \frac{1}{\omega C}\right)}{(R_L + R_C)^2 + \left(\omega L - \frac{1}{\omega C}\right)^2} \quad \text{Eqn. (7)}$$

The optimal transformer ratio $Y_t$ depends on the voltage of the supplied power $V_{ps}$ (V), the maximum current that can be safely drawn from the supplied power Imax (A), and the impedance of the tank circuit $Z_{eq}$ (Ω), and the resistance as seen by the power supply $R_{ps}$ (Ω), as shown below in Equations (8) and (9).

$$R_{ps} = Z_{eq} Y_t^2 = \frac{V_{ps}}{I_{max}} \quad \text{Eqn. (8)}$$

$$Y_t = \sqrt{\frac{V_{ps}}{I_{max} Z_{eq}}} \quad \text{Eqn. (9)}$$

The above equations describe the turn ratio of the transformer 408 that provides the maximum amount of power drawn from the power source 402. If a ratio larger than the ratio shown in Equation 9 is chosen, the current draw from the main power source 402 will be reduced and the overall power consumption of the generator 400 will decrease.

Figure 5:
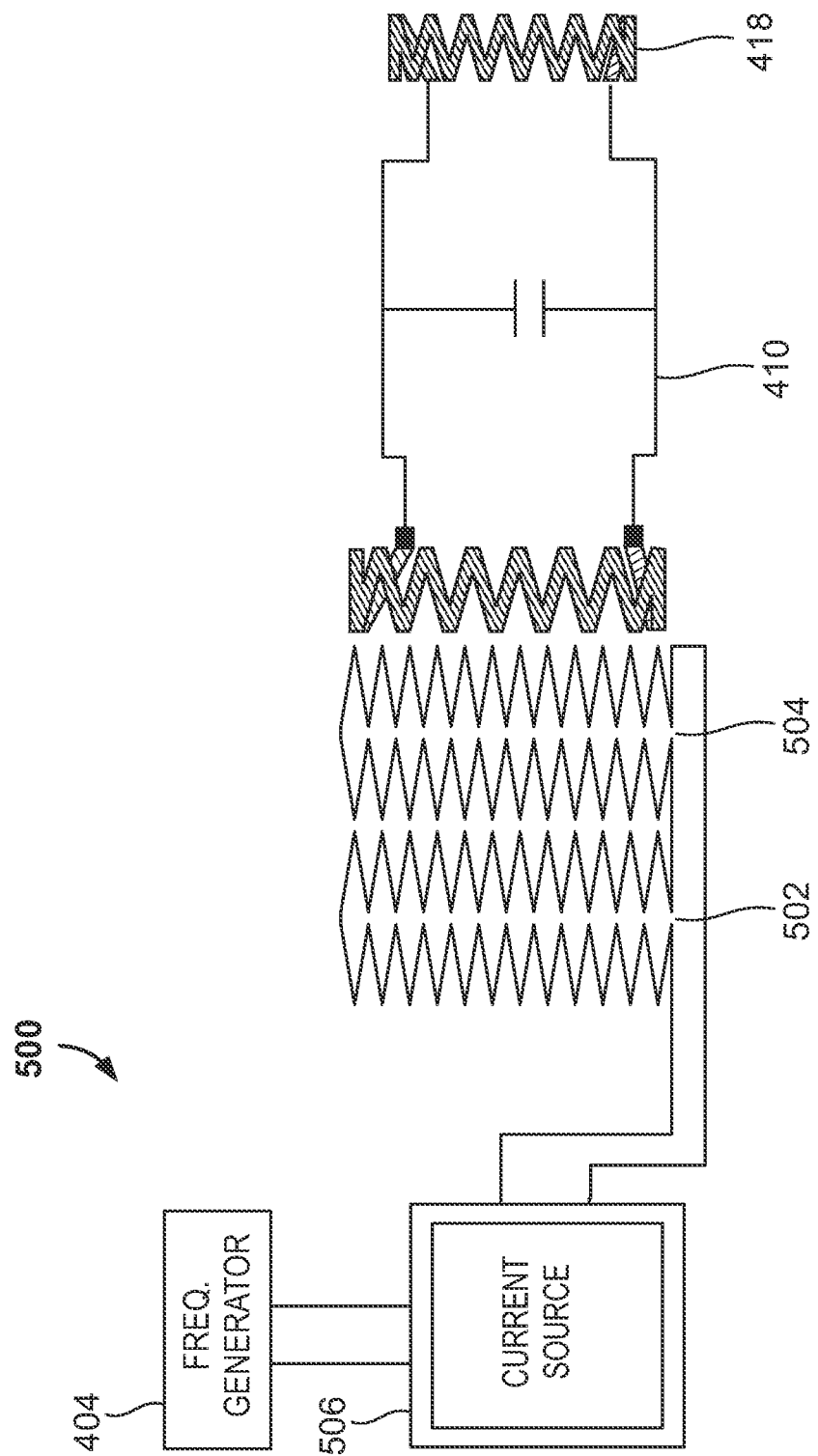
FIG. 5 is a schematic illustration of another example architecture for an electromagnetic field generator.

FIG. 5 illustrates another example circuit architecture for an electromagnetic field generator 500 that may be included, for example, in a medical diagnostic system or automated pipetting system. Components that are similar to components described in other examples will not be repeated here for this example or for subsequent examples, though the values of the components may be different. For example, the current source, frequency, capacitor, etc. may have different values but operate in a similar manner as disclosed above. The example generator 500 of FIG. 5 includes a transformer with a ratio larger than the optimal selection. In this example shown in FIG. 5, a 643 kHz square wave may be generated by the frequency generator 404. A current source 506, which incorporates aspects of the main power source 402 and power controller 406 of FIG. 4, produces, in this example, a current of about 3.3A. The first transformer 502 and the second transformer 504 together form, in this example, a transformer having a turn ratio of about 16:1. Thus, the current multiplication is sixteen times greater after the transformers 502, 504. In this example, the post-transformer current is about 52.8A. The tank circuit 410, in this example, increases the current further to about 160A, resulting in an overall increase of about 48-fold at the work coil 418. In this example, the overall system power is reduced, but the draw on the current source 506 is reduced to match the requirements desired in this example.

Figure 6:
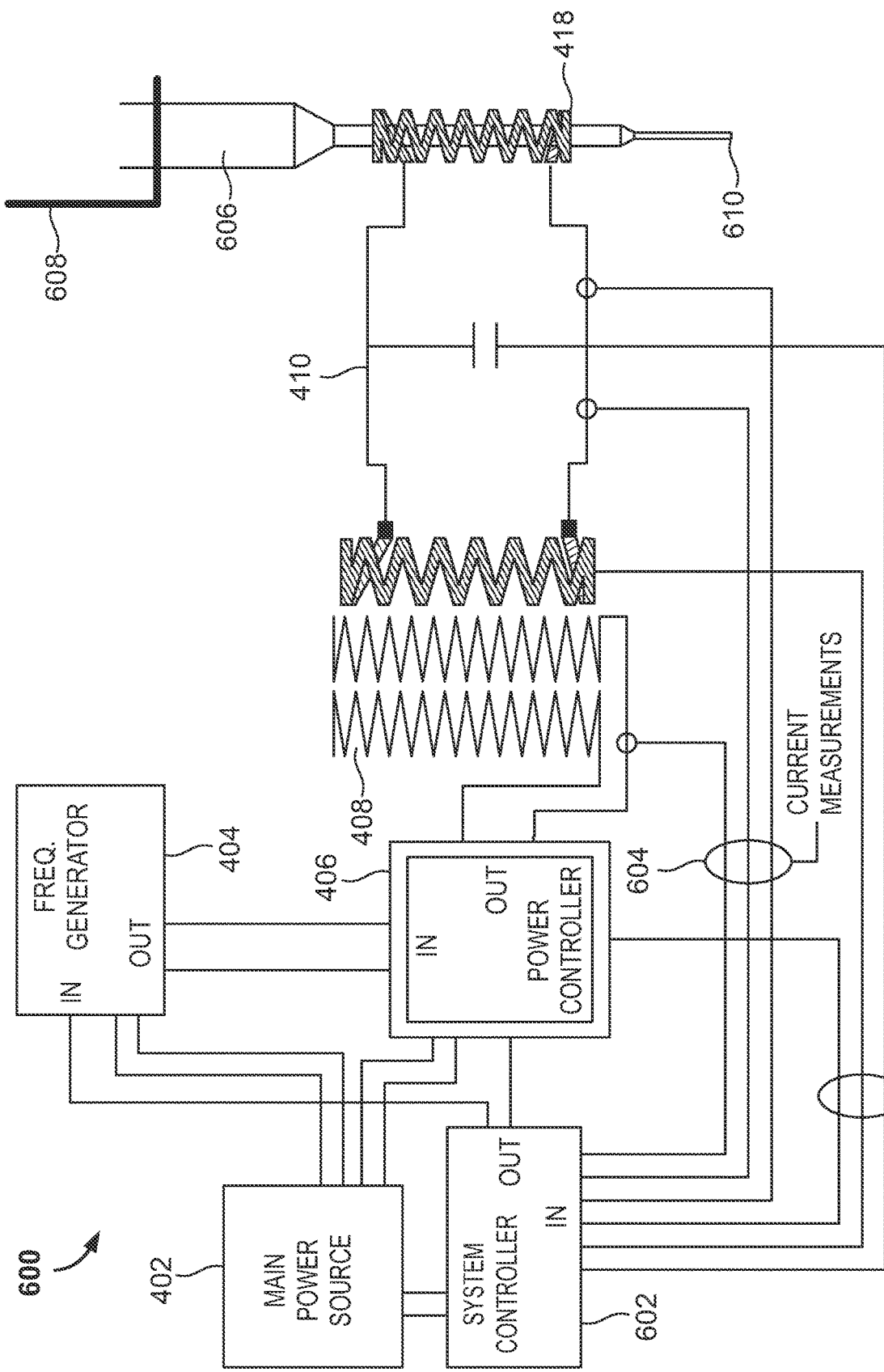
FIG. 6 is a schematic illustration of another example architecture for an electromagnetic field generator.

FIG. 6 illustrates another example circuit architecture for an electromagnetic field generator 600 that may be included, for example, in a medical diagnostic system or automated pipetting system. The example generator 600 of FIG. 6 includes a controller 602 and one or more feedback loop(s) 604. The feedback loop(s) 604 provide data to the controller 602 regarding various metrics of the generator 600 such as, for example, a frequency, an impedance, a temperature, a presence of an aspiration and/or dispense device 606 in the electromagnetic field of the work coil 418, a voltage reading and/or a current reading at any point in the system. The presence or absence of the aspiration and/or dispense device 606 is detectable through temperature or load changes at the work coil 418. In addition, a physical characteristic of the aspiration and/or dispense device 606 may change as an arm 608 moves the aspiration and/or dispense device 606 up or down through the work coil 418 to change the surface of the aspiration and/or dispense device 606 that is disposed in the magnetic field and, therefore, subject to inductive heating. For example, the example aspiration and/or dispense device 606 has a smaller diameter (i.e., is tapered) toward a tip 610. The optimal frequency to adequately heat the tip 610 is different than the frequency needed to adequately heat a portion of the aspiration and/or dispense device 606 with a larger diameter. Thus, the controller 602 may adjust the frequency to change a strength of the electromagnetic field to optimize a heating temperature of the aspiration and/or dispense device 606 based on the data.

The controller 602 also acts as a calibrator to enable the generator 600 to self-calibrate based on drifting of the capacitance or impedance over time. The controller 602 further may also sense shorts and/or other problems with the any components of the generator 600 or interconnections therebetween.

Figure 7:
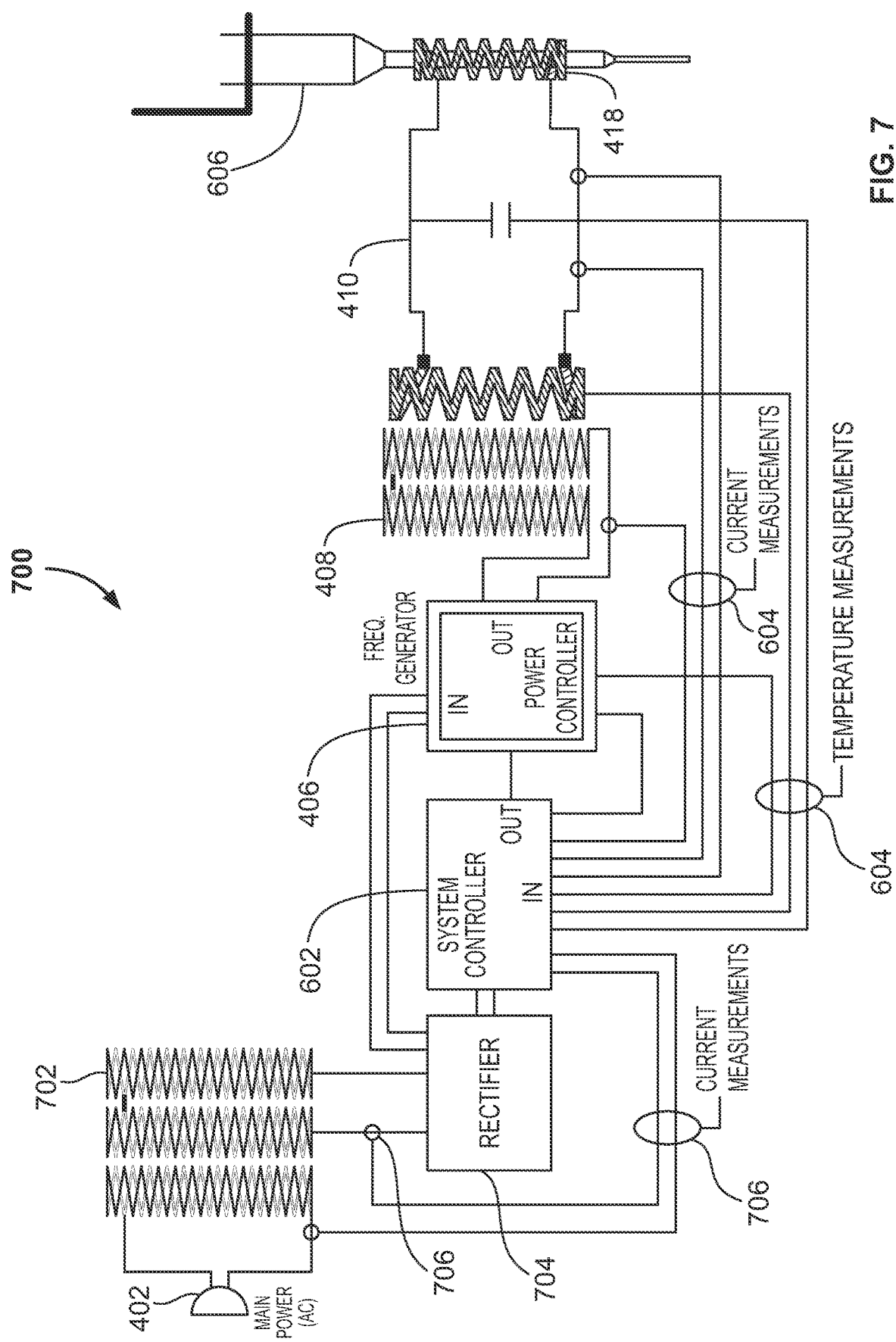
FIG. 7 is a schematic illustration of yet another example architecture for an electromagnetic field generator.

FIG. 7 illustrates another example circuit architecture for an electromagnetic field generator 700 that may be included, for example, in a medical diagnostic system or automated pipetting system. The example generator 700 of FIG. 7 includes a step-up/down transformer 702 coupled to the main power 402 and a rectifier 704. The step-up/down transformer 702 and rectifier 704 are separate components in some examples and are integrated with the power supply 402 in other examples. The step-up/down transformer 702 and the rectifier 704 enable the generator 700 to draw power from the power supply 402 and manipulate that power into a direct current (DC) signal having a suitable voltage and current capacity. Thus, the generator 700 may be coupled to an electrical wall outlet in any country and the step-up/down transformer 702 and rectifier 704 may be selected and/or adjusted to adjust to the power available from the electrical outlet in the wall. Thus, the transformer 702 and/or rectifier 704 may be selected such that the system does not draw excessive current from the main power supply 402. In some examples, the step-up/down transformer 702 and the rectifier 704 modify the power to change the power supply 402 supplied AC voltage to DC voltage, to have a voltage of 120V and 10A of current and/or otherwise adjust the supplied power. The example generator 700 also include additional feedback loops 706 to provide further data to the controller 602 such as, for example, current readings, voltage readings or any other suitable data.

While an example manner of implementing generators 400, 500, 600, 700 has been illustrated in FIGS. 4-7, one or more of the elements, processes and/or devices illustrated in FIGS. 4-7 may be combined, divided, re-arranged, omitted, eliminated and/or implemented in any other way. Further, the example frequency generator 402, power controller 406, current source 506, system controller 602, rectifier 704 and/or, more generally, the example generators 400, 500, 600, 700 of FIGS. 4-7 may be implemented by hardware, software, firmware and/or any combination of hardware, software and/or firmware whether as part of a medical diagnostic device or as a standalone induction heating cleaning device. Thus, for example, any of the example frequency generator 402, power controller 406, current source 506, system controller 602, rectifier 704 and/or, more generally, the example generators 400, 500, 600, 700 of FIGS. 4-7 could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the apparatus or system claims of this patent are read to cover a purely software and/or firmware implementation, at least one of the example, frequency generator 402, power controller 406, current source 506, system controller 602 and/or rectifier 704 are hereby expressly defined to include a tangible computer readable medium such as a memory, DVD, CD, Blu-ray, etc. storing the software and/or firmware. Further still, the example generator 400, 500, 600, 700 of FIGS. 4-7 may include one or more elements, processes and/or devices in addition to, or instead of, those illustrated in FIGS. 4-7, and/or may include more than one of any or all of the illustrated elements, processes and devices.

Figure 8:
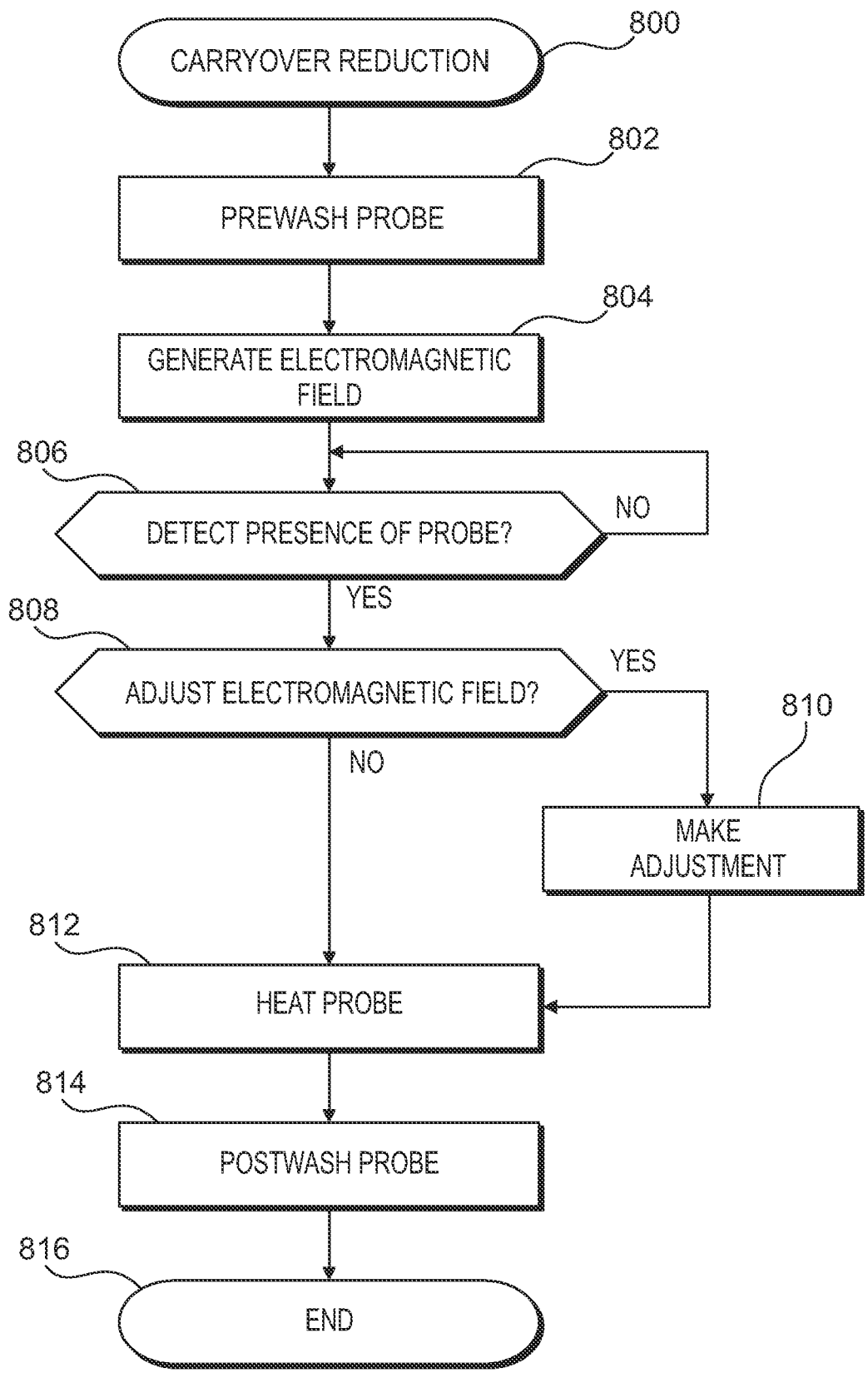
FIG. 8 is a flow chart representative of an example process that may be performed to implement example systems disclosed herein.

A flowchart representative of an example process that may be used to implement the apparatus and systems of FIGS. 1-7 is shown in FIG. 8. In this example, the process comprises a program for execution by a processor such as the processor 912 shown in the example computer 9000 discussed below in connection with FIG. 9. The program may be embodied in software stored on a tangible computer readable medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware. Further, although the example program is described with reference to the flowchart illustrated in FIG. 8, many other methods of implementing the example systems and apparatus disclosed herein may alternatively be used. For example, the order of execution of the blocks may be changed, and/or some of the blocks described may be changed, eliminated, or combined.

As mentioned above, the example process of FIG. 8 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example process of FIG. 8 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 8 illustrates a process 800 of carryover reduction which includes, for example, denaturing and/or deactivating proteins and/or other biological materials, sterilization, cleaning, etc. In some examples, the process 800 includes prewashing or otherwise pretreating a probe or other aspiration and/or dispense device (block 802) using, for example one or more of the prewashes of FIGS. 2 and 3. The example process 800 also includes generating an electromagnetic field (block 804). An example electromagnetic field may be generated by, for example, the coils 100, 204, 306, 418 of FIGS. 1-7 and/or the generators 400, 500, 600, 700 of FIGS. 4-7. In some examples, the electromagnetic field is an alternating electromagnetic field generated by an AC power supply.

In the example process 800 of FIG. 8, the presence or absence of a probe is detected (block 806). If a probe is not detected, control remains at block 806 until a probe has been introduced into the generated electromagnetic field. When a probe has been introduced into the electromagnetic field, the example process 800 determines if the electromagnetic field should be adjusted (block 808). For example, the controller 602 may sense that the dimensions of the probe in the work coil 418 require a different frequency to optimize the electromagnetic field and the resulting induced heat, and the process 800 makes the adjustment (block 810). If no adjustment is necessary or after an adjustment has been made, the process 800 continues, and the probe is heated (block 812). During the heating of the probe (block 812), the position of the probe may be adjusted (e.g., raised or lowered) with respect to the electromagnetic field and the coil to change a portion of the probe that is subjected to the field and the related inductive heating. After the desired temperature and/or duration of heating of the probe to denature and/or deactivate any biological matter, one or more optional postwash steps may occur (block 814). For example, a postwash may rinse the probe of carbonized proteins and/or other residue, a cooling wash may lower the temperature of the probe, and/or other post-treatments may occur. The example process 800 ends (block 816) and the probe is reusable.

Figure 9:
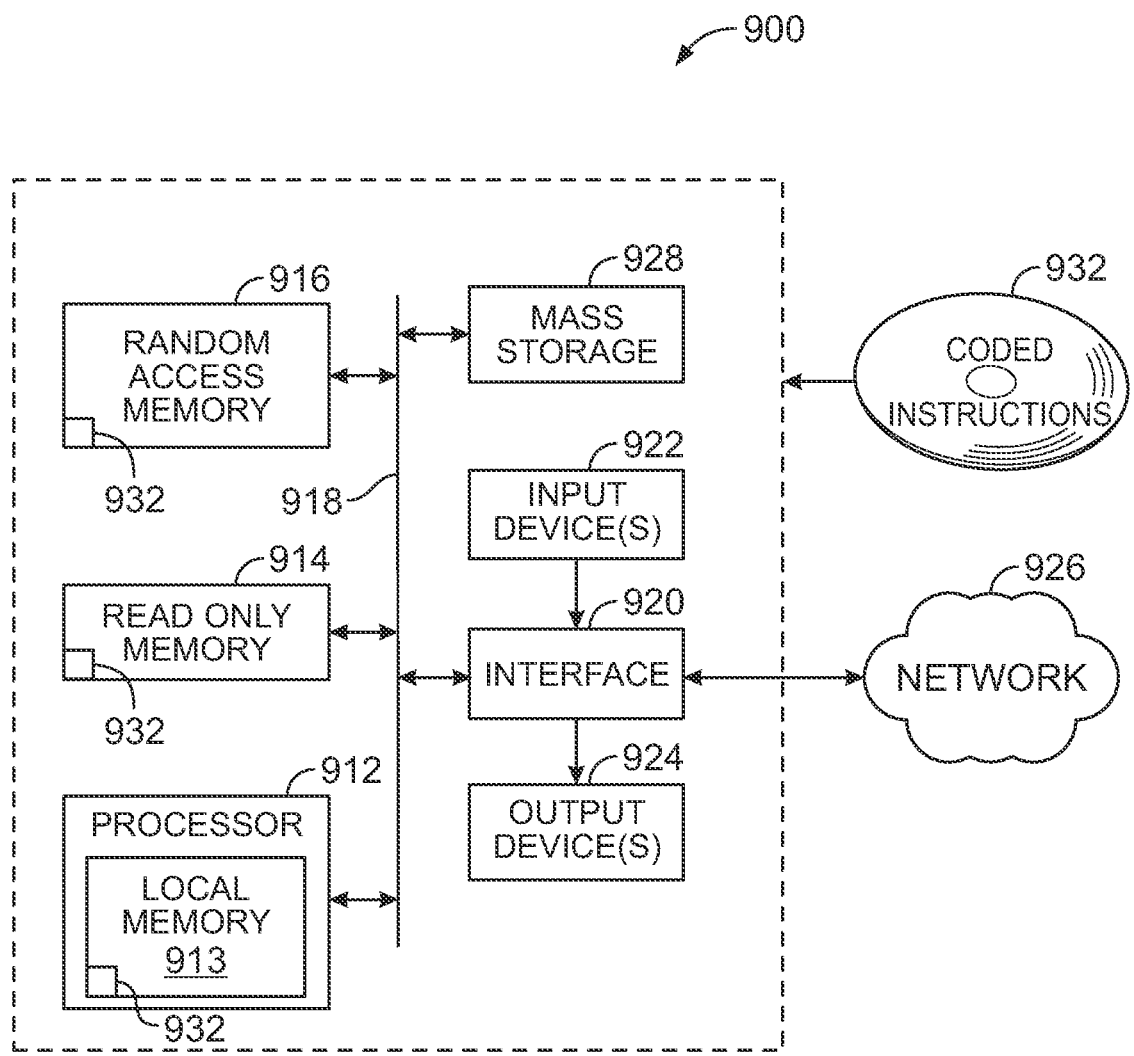
FIG. 9 illustrates an example processor platform that may be used to implement any or all of the example methods, systems and/or apparatus disclosed herein.

FIG. 9 is a block diagram of an example computer 900 capable of executing the process of FIG. 8 to implement the apparatus of FIGS. 1-7. The computer 900 can be, for example, a server, a personal computer, or any other type of computing device.

The system 900 of the instant example includes a processor 912. For example, the processor 912 can be implemented by one or more microprocessors or controllers from any desired family or manufacturer.

The processor 912 includes a local memory 913 (e.g., a cache) and is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller.

The computer 900 also includes an interface circuit 920. The interface circuit 920 may be implemented by any type of interface standard, such as an Ethernet interface, a universal serial bus (USB), and/or a PCI express interface.

One or more input devices 922 are connected to the interface circuit 920. The input device(s) 922 permit a user to enter data and commands into the processor 912. The input device(s) can be implemented by, for example, a keyboard, a mouse, a touchscreen, a track-pad, a trackball, isopoint and/or a voice recognition system.

One or more output devices 924 are also connected to the interface circuit 920. The output devices 924 can be implemented, for example, by display devices (e.g., a liquid crystal display, a cathode ray tube display (CRT), a printer and/or speakers). The interface circuit 920, thus, typically includes a graphics driver card.

The interface circuit 920 also includes a communication device such as a modem or network interface card to facilitate exchange of data with external computers via a network 926 (e.g., an Ethernet connection, a digital subscriber line (DSL), a telephone line, coaxial cable, a cellular telephone system, etc.).

The computer 900 also includes one or more mass storage devices 928 for storing software and data. Examples of such mass storage devices 928 include floppy disk drives, hard drive disks, compact disk drives and digital versatile disk (DVD) drives.

Coded instructions 932 to implement the process 800 of FIG. 8 may be stored in the mass storage device 928, in the volatile memory 914, in the non-volatile memory 916, and/or on a removable storage medium such as a CD or DVD.

From the foregoing, it will appreciated that the above disclosed methods, apparatus, systems and articles of manufacture can be used to inductively heat aspiration and/or dispense devices in medical diagnostic equipment or automated pipetting system. These examples enable the heating of such aspiration and/or dispense devices without requiring physical or electrical contact with the aspiration and/or dispense device. The risk of an electrical short is reduced, and a lower voltage may be used. Also, less heat is required to sterilize, denature or deactivate proteins and other biological matter and/or otherwise clean the aspiration and/or dispense devices. Thus, the time required for the example processes disclosed herein is also reduced. In addition, the heat is controlled and evenly spread through the targeted surface, and the entire aspiration and/or dispense device does not have to be heated. Also, induction heating of the aspiration and/or dispense devices enables the devices to be reused. Induction heating produces negligible solid waste and significantly less biohazardous waste. The example systems and apparatus disclosed herein can be plugged into any electrical wall outlet and do not require dedicated power supply lines for the electromagnetic field generators. Induction heating offers a safe, controllable, fast and low incremental cost method for preventing and/or eliminating carryover or cross contamination of proteins and/or other biological matter.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

The status of the claims:

1. A method comprising:
generating an alternating electromagnetic field by flowing a current though an induction coil;
exposing, via a moveable arm, a sample carrier to the alternating electromagnetic field to cause a property of a biological sample to be adjusted, the biological sample carried by the sample carrier; and
raising or lowering, via the moveable arm, the sample carrier relative to the induction coil; and
adjusting the flow of current through the induction coil responsive to the raising or lowering of the sample carrier.

2. The method of claim 1, further including exposing the sample carrier to a fluid during exposure of the sample carrier to the alternating electromagnetic field.

3. The method of claim 1, further including disposing at least a portion of the sample carrier in a container during exposure of the sample carrier to the alternating electromagnetic field.

4. The method of claim 1, further including detecting a change in the alternating electromagnetic field responsive to a presence of at least a portion of the sample carrier in the alternating electromagnetic field.

5. The method of claim 1, further including washing the sample carrier before exposing the sample carrier to the alternating electromagnetic field.

6. The method of claim 1, wherein the raising or lowering of the sample carrier is to cause (a) a first portion to be exposed to the alternating electromagnetic field at a first time and (b) a second portion of the sample carrier but not the first portion to be exposed to the alternating electromagnetic field at a second time, the second time different than the first time.

7. The method of claim 6, wherein the first portion is surrounded by the induction coil at the first time.

8. The method of claim 1, further including executing an algorithm to control heating of the sample carrier via the alternating electromagnetic field.

9. The method of claim 1, wherein the exposure of the sample carrier to the alternating electromagnetic field is to cause the property of the biological sample to be deactivated or denatured.

10. An apparatus comprising:
means for generating an alternating electromagnetic field;
means for moving a sample carrier, the means for moving to:
cause the sample carrier to be exposed to the alternating electromagnetic field to cause a property of a biological sample to be adjusted, the biological sample carried by the sample carrier; and
raise or lower the sample carrier relative to the means for generating; and
means for controlling, the means for controlling to adjust a flow of current through the means for generating responsive to the raising or lowering of the sample carrier.

11. The apparatus of claim 10, wherein the sample carrier is a probe.

12. The apparatus of claim 10, wherein the means for generating is associated with a diagnostic instrument.

13. The apparatus of claim 10, wherein the exposure of the sample carrier to the alternating electromagnetic field is to cause a temperature of a surface of the sample carrier to change.

14. The apparatus of claim 10, wherein the means for moving is to cause at least a portion of the sample carrier to be disposed in a container during exposure of the sample carrier to the alternating electromagnetic field.

15. The apparatus of claim 10, wherein the means for moving is to cause (a) a first portion to be exposed to the alternating electromagnetic field at a first time and (b) a second portion of the sample carrier but not the first portion to be exposed to the alternating electromagnetic field at a second time, the second time different than the first time.

16. The apparatus of claim 15, wherein the first portion is laterally surrounded by the means for generating at the first time.

17. The apparatus of claim 10, further including means for exposing the sample carrier to a fluid during exposure of the sample carrier to the alternating electromagnetic field.

18. The apparatus of claim 10, wherein the means for controlling is to detect a change in the alternating electromagnetic field responsive to a presence of at least a portion of the sample carrier in the alternating electromagnetic field.

19. The apparatus of claim 10, wherein the exposure of the sample carrier to the alternating electromagnetic field is to cause the property of the biological sample to be deactivated or denatured.

20. The apparatus of claim 10, further including means for washing the sample carrier before exposure of the sample carrier to the alternating electromagnetic field.

* * * * *